US012594091B2

(12) United States Patent

Voic et al.

(10) Patent No.: US 12,594,091 B2

(45) Date of Patent: Apr. 7, 2026

(54) ULTRASONIC SURGICAL INSTRUMENT WITH PROBE AT ANGLE TO HANDPIECE

(71) Applicant: Misonix, LLC, Farmingdale, NY (US)

(72) Inventors: Dan Voic, Cedar Grove, NJ (US); Alexander Darian, Brightwaters, NY (US); Scott Isola, Deer Park, NY (US); Lawrence Agtuca, Holbrook, NY (US)

(73) Assignee: Misonix, LLC, Farmingdale, NY (US)

( * ) Notice: Subject to any disclaimer, the term of this patent is extended or adjusted under 35 U.S.C. 154(b) by 967 days.

(21) Appl. No.: 17/571,101

(22) Filed: Jan. 7, 2022

(65) Prior Publication Data

US 2023/0210549 A1 Jul. 6, 2023

Related U.S. Application Data

(60) Provisional application No. 63/296,073, filed on Jan. 3, 2022.

(51) Int. Cl.
A61B 17/32 (2006.01)

(52) U.S. Cl.
CPC ................. A61B 17/320068 (2013.01); *A61B 2017/320082* (2017.08)

(58) Field of Classification Search
CPC ............ A61B 17/320068; A61B 2017/320082
See application file for complete search history.

(56) References Cited

U.S. PATENT DOCUMENTS 2,349,959 A 5/1944 Edward
2,753,666 A 7/1956 Sasse 3,368,280 A 2/1968 Friedman et al.
3,680,610 A 8/1972 Lindgren
3,805,787 A 4/1974 Banko
4,188,952 A 2/1980 Loschilov et al.
(Continued)

FOREIGN PATENT DOCUMENTS

CN 101511286 A 8/2009
CN 210249992 U 4/2020
(Continued)

OTHER PUBLICATIONS

International Preliminary Report on Patentability for Application No. PCT/US2023/010008, dated Jul. 18, 2024, 9 pages.
(Continued)

*Primary Examiner* — Ashley L Fishback

(57) ABSTRACT

An ultrasonic surgical instrument includes a handpiece casing and an electromechanical transducer assembly disposed inside the handpiece casing, where the transducer assembly includes a front driver and the transducer assembly has a longitudinal axis. A probe is operatively connected to the front driver at an acute angle to the longitudinal axis of the transducer assembly. A sheath surrounds the probe and is connected at a proximal end to the handpiece casing. The sheath is attached to the casing by a twist quick release coupling. A diaphragm seal inside the proximal end of the sheath blocks liquid irrigant in a cylindrical space between the sheath and the probe from penetrating proximally of a port feeding irrigant to the space. The front driver is geometrically configured to enable an angled connection of probe to handpiece proximate a nodal plane.

21 Claims, 5 Drawing Sheets

(56) References Cited

U.S. PATENT DOCUMENTS

| | | | |
|---|---|---|---|
| 4,425,115 A | 1/1984 | Wuchinich |
| 4,804,364 A | 2/1989 | Dieras et al. |
| 4,988,334 A | 1/1991 | Hornlein et al. |
| 5,163,433 A | 11/1992 | Kagawa et al. |
| 5,176,677 A | 1/1993 | Wuchinich |
| 5,180,363 A | 1/1993 | Idemoto et al. |
| 5,222,937 A | 6/1993 | Kagawa |
| 5,261,922 A | 11/1993 | Hood |
| 5,312,329 A | 5/1994 | Beaty et al. |
| 5,342,380 A | 8/1994 | Hood |
| 5,465,468 A | 11/1995 | Manna |
| 5,484,398 A | 1/1996 | Stoddard |
| 5,517,889 A | 5/1996 | Logan |
| 5,527,273 A | 6/1996 | Manna et al. |
| 5,531,597 A | 7/1996 | Foulkes et al. |
| 5,695,510 A | 12/1997 | Hood |
| 5,769,211 A | 6/1998 | Manna et al. |
| 5,906,595 A | 5/1999 | Powell et al. |
| 5,935,142 A | 8/1999 | Hood |
| 5,935,143 A | 8/1999 | Hood |
| 5,976,105 A | 11/1999 | Marcove et al. |
| 6,033,375 A | 3/2000 | Brumbach |
| 6,036,667 A | 3/2000 | Manna et al. |
| 6,256,859 B1 | 7/2001 | Stoddard et al. |
| 6,270,471 B1 | 8/2001 | Hechel et al. |
| 6,352,532 B1 | 3/2002 | Kramer et al. |
| 6,375,648 B1 | 4/2002 | Edelman et al. |
| 6,379,371 B1 | 4/2002 | Novak et al. |
| 6,436,114 B1 | 8/2002 | Novak et al. |
| 6,443,969 B1 | 9/2002 | Novak et al. |
| 6,454,730 B1 | 9/2002 | Hechel et al. |
| 6,461,314 B1 | 10/2002 | Pant et al. |
| 6,492,762 B1 | 12/2002 | Pant et al. |
| 6,494,714 B1 | 12/2002 | Copeland |
| 6,582,440 B1 | 6/2003 | Brumbach |
| 6,602,248 B1 | 8/2003 | Sharps et al. |
| 6,613,056 B1 | 9/2003 | Brumbach et al. |
| 6,648,839 B2 | 11/2003 | Manna et al. |
| 6,736,814 B2 | 5/2004 | Manna et al. |
| 6,787,974 B2 | 9/2004 | Fjield et al. |
| 6,799,729 B1 | 10/2004 | Voic |
| 6,869,439 B2 | 3/2005 | White et al. |
| 6,902,536 B2 | 6/2005 | Manna et al. |
| 7,025,735 B2 | 4/2006 | Soring et al. |
| 7,223,267 B2 | 5/2007 | Isola et al. |
| 7,431,704 B2 | 10/2008 | Babaev |
| 7,442,168 B2 | 10/2008 | Novak et al. |
| 7,494,488 B2 | 2/2009 | Weber |
| 7,522,955 B2 | 4/2009 | Rontal |
| 7,608,054 B2 | 10/2009 | Söring et al. |
| 7,717,913 B2 | 5/2010 | Novak et al. |
| 7,776,027 B2 | 8/2010 | Manna et al. |
| 7,785,278 B2 | 8/2010 | Babaev |
| D627,463 S | 11/2010 | Voic et al. |
| 7,905,854 B2 | 3/2011 | Hazut et al. |
| 7,931,611 B2 | 4/2011 | Novak et al. |
| D644,326 S | 8/2011 | Voic et al. |
| 8,025,672 B2 | 9/2011 | Novak et al. |
| 8,109,925 B2 | 2/2012 | Voic et al. |
| 8,221,424 B2 | 7/2012 | Cha |
| D667,117 S | 9/2012 | Darian et al. |
| 8,343,178 B2 | 1/2013 | Novak et al. |
| 8,348,880 B2 | 1/2013 | Messerly et al. |
| 8,353,912 B2 | 1/2013 | Darian et al. |
| D680,218 S | 4/2013 | Darian et al. |
| 8,430,897 B2 | 4/2013 | Novak et al. |
| 8,562,547 B2 | 10/2013 | Babaev |
| 8,659,208 B1 | 2/2014 | Rose et al. |
| 8,690,783 B2 | 4/2014 | Sinelnikov |
| 8,698,377 B2 | 4/2014 | Sinelnikov |
| 8,814,870 B2 | 8/2014 | Paraschiv et al. |
| 8,888,783 B2 | 11/2014 | Young |
| 8,894,673 B2 | 11/2014 | Darian |
| 8,961,547 B2 | 2/2015 | Dietz et al. |
| 9,070,856 B1 | 6/2015 | Rose et al. |
| 9,211,137 B2 | 12/2015 | Voic |
| 9,226,767 B2 | 1/2016 | Stulen et al. |
| 9,320,528 B2 | 4/2016 | Voic et al. |
| 9,387,005 B2 | 7/2016 | Voic |
| 9,603,656 B1 | 3/2017 | Germain et al. |
| 9,622,766 B2 | 4/2017 | Voic |
| 9,636,187 B2 | 5/2017 | Voic |
| 9,693,792 B2 | 7/2017 | Novak et al. |
| 9,763,673 B2 | 9/2017 | Young |
| 9,861,446 B2 | 1/2018 | Lang |
| 9,872,697 B2 | 1/2018 | Voic |
| 9,949,751 B2 | 4/2018 | Voic |
| 9,962,182 B2 | 5/2018 | Dietz et al. |
| 10,016,208 B2 | 7/2018 | Gouery et al. |
| 10,076,349 B2 | 9/2018 | Voic |
| 10,092,308 B2 | 10/2018 | Mikus et al. |
| 10,092,741 B2 | 10/2018 | Darian |
| 10,117,666 B2 | 11/2018 | Voic |
| 10,182,837 B2 | 1/2019 | Isola et al. |
| 10,206,704 B2 | 2/2019 | Voic et al. |
| 10,299,809 B2 | 5/2019 | Mikus et al. |
| 10,398,463 B2 | 9/2019 | Darian et al. |
| 10,398,465 B2 | 9/2019 | Darian |
| 10,405,875 B2 | 9/2019 | Voic et al. |
| 10,463,381 B2 | 11/2019 | Voic et al. |
| 10,470,788 B2 | 11/2019 | Sinelnikov |
| 10,470,789 B2 | 11/2019 | Mikus et al. |
| 10,471,281 B2 | 11/2019 | Mikus |
| 10,543,012 B2 | 1/2020 | Pantano |
| 10,588,691 B2 | 3/2020 | Pellegrino et al. |
| 10,639,733 B2 | 5/2020 | Campbell et al. |
| 10,687,824 B2 | 6/2020 | Shiels et al. |
| 10,835,276 B2 | 11/2020 | Voic et al. |
| 10,842,587 B2 | 11/2020 | Mikus et al. |
| 11,007,308 B2 | 5/2021 | Payne et al. |
| 11,298,434 B2 | 4/2022 | Isola et al. |
| 11,317,936 B2 * | 5/2022 | James ............ A61B 17/320068 |
| 11,324,531 B2 | 5/2022 | Voic et al. |
| 11,389,183 B2 | 7/2022 | Voic et al. |
| 11,406,413 B2 | 8/2022 | Voic et al. |
| 11,540,853 B2 | 1/2023 | Voic et al. |
| 11,672,558 B2 | 6/2023 | Voic |
| 11,737,775 B2 | 8/2023 | Voic et al. |
| 11,950,790 B2 | 4/2024 | Voic |
| 12,011,190 B2 | 6/2024 | Theodore et al. |
| 12,279,787 B2 | 4/2025 | Ellegala |
| 2001/0029370 A1 | 10/2001 | Hodva et al. |
| 2003/0212395 A1 | 11/2003 | Woloszko et al. |
| 2004/0265776 A1 | 12/2004 | Tipton et al. |
| 2005/0033292 A1 | 2/2005 | Teitelbaum et al. |
| 2006/0030797 A1 | 2/2006 | Zhou et al. |
| 2006/0235305 A1 | 10/2006 | Cotter et al. |
| 2006/0241533 A1 | 10/2006 | Geller |
| 2007/0060926 A1 | 3/2007 | Escaf |
| 2007/0213734 A1 | 9/2007 | Bleich et al. |
| 2008/0015551 A1 | 1/2008 | Feine |
| 2008/0057470 A1 | 3/2008 | Levy et al. |
| 2008/0058775 A1 | 3/2008 | Darian et al. |
| 2008/0108985 A1 | 5/2008 | Konesky |
| 2008/0183173 A1 | 7/2008 | Jozat |
| 2008/0234709 A1 | 9/2008 | Houser |
| 2008/0234710 A1 | 9/2008 | Neurohr et al. |
| 2009/0143678 A1 | 6/2009 | Keast et al. |
| 2009/0247937 A1 | 10/2009 | Rontal |
| 2010/0022944 A1 | 1/2010 | Wilcox |
| 2010/0049188 A1 | 2/2010 | Nelson et al. |
| 2010/0076349 A1 | 3/2010 | Babaev |
| 2011/0092880 A1 | 4/2011 | Gertner |
| 2011/0105958 A1 | 5/2011 | Babaev |
| 2011/0160624 A1 | 6/2011 | Babaev |
| 2011/0264090 A1 | 10/2011 | Shadduck et al. |
| 2012/0014868 A1 | 1/2012 | Roy |
| 2012/0053492 A1 | 3/2012 | Chang et al. |
| 2013/0103021 A1 | 4/2013 | Germain et al. |
| 2013/0123774 A1 | 5/2013 | Zadeh |
| 2013/0209955 A1 | 8/2013 | Moran et al. |
| 2013/0226042 A1 | 8/2013 | Novak et al. |
| 2013/0231528 A1 | 9/2013 | Voic |
| 2013/0245638 A1 | 9/2013 | Horton et al. |

(56) References Cited

U.S. PATENT DOCUMENTS

| | | |
|---|---|---|
| 2014/0107537 A1 | 4/2014 | Beaupre |
| 2014/0180002 A1 | 6/2014 | Voic |
| 2014/0277030 A1 | 9/2014 | Lauchner |
| 2014/0277034 A1 | 9/2014 | Darian |
| 2014/0350567 A1 | 11/2014 | Schmitz et al. |
| 2014/0358043 A1 | 12/2014 | Akagane |
| 2015/0045701 A1 | 2/2015 | Akagane |
| 2015/0066032 A1 | 3/2015 | Young |
| 2015/0088137 A1 | 3/2015 | Manna |
| 2015/0094723 A1 | 4/2015 | Darian |
| 2015/0157387 A1 | 6/2015 | OuYang et al. |
| 2015/0164534 A1 | 6/2015 | Felder et al. |
| 2015/0297246 A1 | 10/2015 | Patel et al. |
| 2016/0022283 A1 | 1/2016 | Wallace et al. |
| 2016/0135835 A1 | 5/2016 | Onuma |
| 2016/0166276 A1 | 6/2016 | Huang et al. |
| 2016/0175150 A1 | 6/2016 | Banko |
| 2016/0206302 A1 | 7/2016 | Eckermann |
| 2016/0222526 A1 | 8/2016 | Rubinsky et al. |
| 2016/0331439 A1 | 11/2016 | Winkelman et al. |
| 2016/0354559 A1 | 12/2016 | Gavini et al. |
| 2017/0340339 A1 | 11/2017 | Madan et al. |
| 2018/0008138 A1 | 1/2018 | Thommen et al. |
| 2019/0000553 A1 | 1/2019 | Lightcap et al. |
| 2019/0307529 A1 | 10/2019 | Jacoby |
| 2020/0121374 A1 | 4/2020 | Mcgahan et al. |
| 2020/0178999 A1 | 6/2020 | Stabilini et al. |
| 2020/0205850 A1 | 7/2020 | Cao et al. |
| 2020/0246056 A1 | 8/2020 | Bonn |
| 2020/0352590 A1 | 11/2020 | Drewek |
| 2020/0405501 A1 | 12/2020 | Orozco Castillo |
| 2021/0145531 A1 | 5/2021 | Gee et al. |
| 2021/0228218 A1 | 7/2021 | Hauser et al. |
| 2023/0048993 A1 | 2/2023 | Levy et al. |

FOREIGN PATENT DOCUMENTS

| | | |
|---|---|---|
| CN | 109152577 B | 1/2022 |
| EP | 2745797 A1 | 6/2014 |
| EP | 2635192 B1 | 3/2019 |
| JP | H0614934 A | 1/1994 |
| JP | H10127682 A | 5/1998 |
| JP | 2019517856 A | 6/2019 |
| KR | 20120093654 A | 8/2012 |
| WO | WO-2000071043 A1 | 11/2000 |
| WO | WO-2001035812 A2 | 5/2001 |
| WO | WO-2004060141 A2 | 7/2004 |
| WO | WO-2007049718 A1 | 5/2007 |
| WO | WO-2007143686 A2 | 12/2007 |
| WO | WO-2008014258 A2 | 1/2008 |
| WO | WO-2008017909 A1 | 2/2008 |
| WO | WO-2008118708 A2 | 10/2008 |
| WO | WO-2008118709 A1 | 10/2008 |
| WO | WO-2009035508 A1 | 3/2009 |
| WO | WO-2009098664 A2 | 8/2009 |
| WO | WO-2009105628 A2 | 8/2009 |
| WO | WO-2010109447 A1 | 9/2010 |
| WO | WO-2013062118 A1 | 5/2013 |
| WO | WO-2014024550 A1 | 2/2014 |
| WO | WO-2014210163 A1 | 12/2014 |
| WO | WO-2014210273 A1 | 12/2014 |
| WO | WO-2015045198 A1 | 4/2015 |
| WO | WO-2015046349 A1 | 4/2015 |
| WO | WO-2015047812 A1 | 4/2015 |
| WO | WO-2015145444 A2 | 10/2015 |
| WO | WO-2015188735 A1 | 12/2015 |
| WO | WO-2017180493 A1 | 10/2017 |
| WO | WO-2017192288 A1 | 11/2017 |
| WO | WO-2018022311 A1 | 2/2018 |
| WO | WO-2018165004 A1 | 9/2018 |
| WO | WO-2019095831 A1 | 5/2019 |
| WO | WO-2019204641 A1 | 10/2019 |
| WO | WO-2022087523 A1 | 4/2022 |
| WO | WO-2022245499 A1 | 11/2022 |
| WO | WO-2023018863 A1 | 2/2023 |
| WO | WO-2023130103 A1 | 7/2023 |

OTHER PUBLICATIONS

International Search Report and Written Opinion for Application No. PCT/US2023/010008, dated May 9, 2023, 12 pages.

SonicOne O.R., Ultrasonic Surgical Debridement. Brochure [online]. Misonix Ultrasonic Surgical Devices, 2012. Retrieved from the Internet: <URL: https://web.archive.org/web/20150218182717/http://www.misonix.com:80/wp-content/uploads/2013/11/SO-OR_2003-12_REV_A_SonicOne_OR_Brochure.pdf>, 6 pages.

SonicOne Plus, Ultrasonic Debridement System. Brochure [online]. Misonix Ultrasonic Surgical Devices, 2013. Retrieved from the Internet: <URL: https://pdf.medicalexpo.com/pdf/misonix/sonicone-plus/79244-106567.html>, 4 pages.

EP Application No. 23735176.2, Extended European Search Report mailed Nov. 25, 2025; Applicant Misonix, LLC; 9 pages.

* cited by examiner

ULTRASONIC SURGICAL INSTRUMENT WITH PROBE AT ANGLE TO HANDPIECE

CROSS-REFERENCE TO RELATED APPLICATIONS

This application claims priority to and the benefit of U.S. Provisional Application Ser. No. 63/296,073, filed on Jan. 3, 2022, the content of which is hereby incorporated by reference in its entirety.

BACKGROUND OF THE INVENTION

This invention relates to an ultrasonic tool or instrument for use in medical surgical procedures.

Ultrasonic tools have become increasingly used in surgical procedures. Ultrasonic ablation tools are recognized for their accuracy, reliability and ease of use. Ultrasonic bone cutting blades may be designed to facilitate the cutting of bone without damage to adjacent soft tissues. See U.S. Pat. No. 8,343,178. Ultrasonic debriders remove necrotic or otherwise damaged tissue without harming underlying healthy tissue. Ultrasonic instruments such as debriders can have integrated tissue treatment modalities such as high-energy electrical current transmission for cauterization (see U.S. Pat. No. 6,648,839) and low-energy electrical energy transmission for pain suppression (U.S. Patent Application Publication No. 2008/0146921) or stimulating tissue repair (U.S. Pat. No. 8,025,672).

Ultrasonic instruments can incorporate probes with bent shafts for facilitating access to troublesome locations. In some surgical procedures, it is advantageous to have the operative head or end effector portion of the probe angled to one side of the shaft to further facilitate access to a desired surgical site. See U.S. Pat. No. 10,398,463. Alternatively, the probe may be straight throughout and attached to the handpiece at an angle. See U.S. Pat. Nos. 5,312,329 and 5,484,398.

In developing a new set of ultrasonic instruments where a handpiece may be utilizable with different probes that may have different end effectors and different surgical capabilities, the present applicant encountered some surprising problems. With a rigid sheath defining an annular liquid flow path between the sheath and a probe, a user placing one hand on the sheath just distal of the handpiece occasionally felt a burning or stinging sensation in that hand. It was eventually discovered that experiencing the sensation depended on the compressive pressure one applied to the sheath with the hand.

Another problem was to design the handpiece and the proximal ends of the probes to facilitate the removal of a probe and the attachment of a different tool so that the changeover could be accomplished readily in the operating room. One might wish, for example, to change from a bone-cutting instrument to an abrading or debriding instrument during a spinal procedure.

Other problems included optimizing efficiency of ultrasonic energy transfer from the transducer array of the handpiece to the probe, not a straightforward task given the angled relationship between the two instrument parts.

OBJECTS OF THE INVENTION

It is an object of the present invention to provide an improved ultrasonic tool or instrument that is effective for use in minimally invasive surgical procedures.

Another object of the present invention is to provide such an improved ultrasonic tool or instrument that has a probe extending at an angle relative to a handpiece.

It is a more particular object of the present invention to provide such a tool or instrument with a sheath around the probe and liquid flow between the two, wherein the risk of painful sensation when holding the sheath during a procedure is reduced or eliminated.

Another object of the present invention is to provide such a tool or instrument where the probe is easily attached to and removed from the handpiece.

A further object of the present invention is to provide such a tool or instrument structured to efficiently transmit ultrasonic mechanical vibratory energy from the handpiece to the probe.

These and other objects of the present invention will be apparent from the descriptions and drawings herein. Although all of the objects of the invention are achieved by one or more embodiments of the invention, there is not necessarily any single embodiment that achieves all of the objects of the invention.

SUMMARY OF THE INVENTION

An ultrasonic surgical instrument comprises, in accordance with the present invention, a handpiece casing and an electromechanical transducer assembly disposed inside the handpiece casing, where the transducer assembly includes a front driver and the transducer assembly has a longitudinal axis. The instrument further comprises a probe operatively connected to the front driver at an acute angle to the longitudinal axis of the transducer assembly (and, typically, the handpiece casing). The probe has a distal end provided with an end effector such as a blade or debriding surface. A sheath surrounds the probe and is connected at a proximal end to the handpiece casing, while the end effector extends distally of a distal tip of the sheath. The sheath is provided at a proximal end with an annular sealing member engaging a distal surface of the handpiece casing. The proximal end of the sheath and the distal end of the handpiece casing are provided with at least two first closure elements and a like number of second closure elements. The first closure elements are provided on either the distal surface of the handpiece casing or the proximal end of the sheath, while the second closure elements are disposed on the proximal end of the sheath or the distal surface of the handpiece casing. The first closure elements each take the form of a projection extending in a radial direction (inwardly from outer member or outwardly from the inner member), whereas the second closure elements each assume the form of an annular open channel or groove having one end that is tapered and defined by a camming surface.

Preferably, the annular sealing member is made of a resiliently compressible material of a suitable surface coefficient of friction. The first closure elements and the second closure elements are configured to frictionally lock the sheath to the handpiece casing by compression of the annular sealing member. The locking and the unlocking of the sheath to the handpiece casing are accomplished by twisting the sheath in opposed directions relative to the handpiece. Thus the camming mechanism enables a quick coupling of the sheath to the handpiece, and a quick decoupling as well.

Accordingly, the handpiece casing is preferably fixed to the sheath by only one locking mechanism, which comprises the annular sealing member, the first closure elements, and the second closure elements.

The projections may take the particular form of annular ribs extending in a plane transverse to an axis of the sheath. The camming surfaces are located along a distal side of the annular open channels and face in a proximal direction towards the handpiece casing.

An ultrasonic surgical instrument pursuant to the present invention comprises a handpiece casing and an electromechanical transducer assembly disposed inside the handpiece casing, the transducer assembly including a front driver and the transducer assembly having a longitudinal axis. A probe is operatively connected to the front driver at an acute angle to the longitudinal axis, the probe having a distal end provided with an end effector. A sheath surrounds the probe and is connected at a proximal end to the handpiece casing so that the end effector extends distally of a distal tip of the sheath. The sheath is provided proximate the proximal end with a port connectable to a source of pressurized liquid coolant for flowing the pressurized liquid coolant into a tubular space between the probe and an inner surface of the sheath. A diaphragm seal is disposed inside the proximal end of the sheath proximally of the port, the diaphragm seal having an annular outer surface in liquid-tight contact with the inner surface of the sheath. The diaphragm is provided at a distal end with an annular inwardly extending flange circumferentially engaging an outer surface of the probe in a liquid-tight seal. The annular inwardly extending flange preferably engages the outer surface of the probe at a node of ultrasonic wave transmission.

The diaphragm in its entirety is preferably spaced from the probe except at the annular inwardly extending flange. The diaphragm seal eliminates the occasional painful or distracting sensation when a user grasps the proximal end portion of the sheath, as described above.

In accordance with another feature of the present invention, the diaphragm is provided at a proximal end with an annular outwardly extending flange clamped between a proximal end surface of the sheath and a distal end surface of the handpiece casing.

According to another feature of the present invention, the sheath has a main body at a proximal end made of rigid material, the sheath further comprising a distal end portion made of silicone polymer.

An ultrasonic surgical instrument in accordance with the invention comprises a handpiece casing and an electromechanical transducer assembly disposed inside the handpiece casing, the transducer assembly including a front driver, and further comprises a probe operatively connected to the front driver at an acute angle to the longitudinal axis, where the probe has a distal end provided with an end effector or operative head. The front driver has an outwardly projecting annular flange and is formed at a distal end with a first cylindrical outer surface coaxial with the longitudinal axis of the transducer assembly. The front driver has a second cylindrical outer surface at the distal end on a side opposed to the first cylindrical outer surface, the second cylindrical outer surface being coaxial with a longitudinal axis of the probe.

Pursuant to a further feature of the present invention, the front driver has two mutually parallel planar outer surfaces extending parallel to the longitudinal axis of the transducer assembly, each of the two mutually parallel planar outer surfaces being contiguous with the first cylindrical outer surface and the second cylindrical outer surface.

The handpiece casing is preferably formed at a distal end with a cylindrical first internal surface coaxial with the longitudinal axis of the transducer assembly and further formed with a cylindrical second internal surface coaxial with the longitudinal axis of the probe.

An ultrasonic surgical instrument comprises, in accordance with the present invention, a handpiece casing and an electromechanical transducer assembly disposed inside the handpiece casing, the transducer assembly including a front driver having an internally threaded receptacle at a distal end. A tubular member extends through the transducer assembly to a proximal end of the internally threaded receptacle. A probe having a longitudinal bore is operatively connected to the front driver at an acute angle to a longitudinal axis of the transducer assembly, the probe having a distal end provided with an end effector. The internally threaded receptacle receives an externally threaded connector at the proximal end of the probe and has a proximal end surface disposed at the acute angle relative to the longitudinal axis of the transducer assembly. A sheath surrounds the probe and is connected at a proximal end to the handpiece casing, the end effector extending distally of a distal tip of the sheath. The tubular member has a lumen with a uniform cross-section including at a distal end opening of the lumen. The bore of the probe has a proximal end opening of smaller cross-section than that of the tubular member. The bore of the probe is aligned with the distal end opening of the tubular member. The tubular member and the bore together define a continuous lumen, the lumen having no shoulder facing in a distal direction at a junction of the tubular member and the bore.

A cradle for use in manually attaching an ultrasonic probe to a handpiece at an acute angle relative to an axis of the handpiece comprises, pursuant to the present invention, a frame and a support on the frame defining the acute angle relative to a bottom side of the frame. The frame has a stop at one end of the frame, the stop being engageable with a front end of the handpiece. The stop has an opening allowing user access to a front driver of a transducer assembly housed within the handpiece. Two wings extend in opposed directions from the frame at the bottom side thereof so as to contact a flat surface on which the frame is placed.

DETAILED DESCRIPTION

Figures 1, 2:
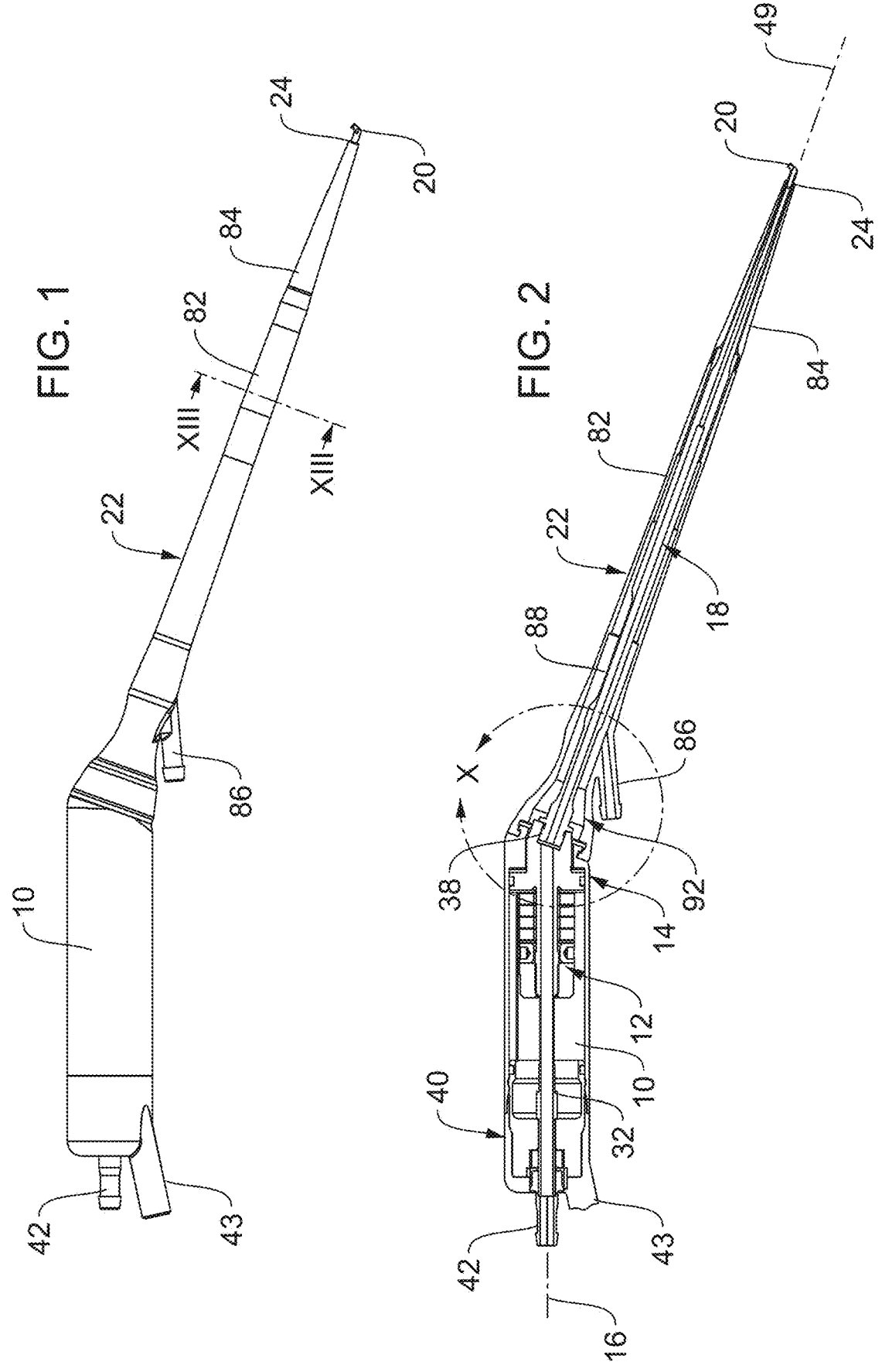
FIG. 1 is a side elevational view of an ultrasonic surgical instrument in accordance with the present invention.
FIG. 2 is a longitudinal cross-sectional view taken parallel to the plane of the drawing in FIG. 1.
Figures 3, 4, 5, 10:
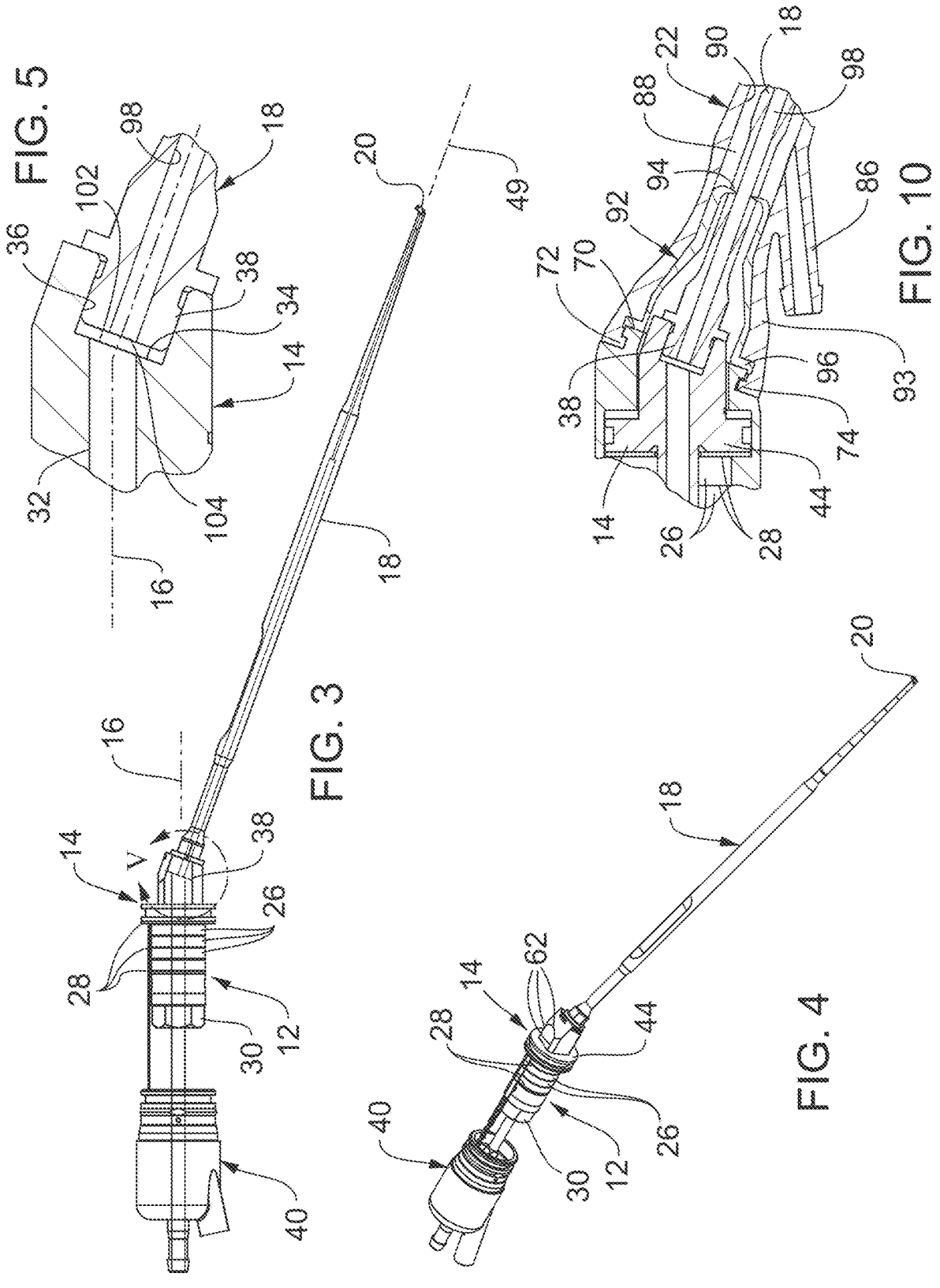
FIG. 3 is a longitudinal cross-sectional view coplanar with the view of FIG. 2, showing a probe and a transducer array that is located within a handpiece casing shown in FIGS. 1 and 2.
FIG. 4 is a front, side and top perspective view of the operative structures shown in FIG. 3, namely, the probe and the transducer array, as well as a proximal end cap assembly of the handpiece casing.
FIG. 5 is a partial longitudinal cross-sectional view, on an enlarged scale, of portion V of FIG. 3, showing a probe-to-transducer coupling.
FIG. 10 is a partial longitudinal cross-sectional view, on an enlarged scale, of portion X of FIG. 2, showing a diaphragm seal and a sheath-to-casing coupling.

As illustrated in FIGS. 1 and 2, an ultrasonic surgical instrument comprises a handpiece casing 10 and an electro-mechanical transducer assembly 12 disposed inside the casing, where the transducer assembly includes a front driver 14 and has a longitudinal axis 16 (FIGS. 3 and 5). The instrument further comprises a probe 18 typically made of a metal alloy and operatively connected to front driver 14 at an acute angle exemplarily of 20° to longitudinal axis 16 of transducer assembly 12. Transducer assembly 12 is preferably positioned symmetrically within casing 10 so that axis 16 serves also as a longitudinal axis of symmetry of the casing. Probe 18 has a distal end (not separately designated) provided with an end effector 20 such as a bone-cutting blade (not illustrated) or a debriding head (shown). A sheath 22 surrounds probe 18 except for end effector or operative head 20 and is connected at a proximal end to handpiece casing 10. End effector or operative head 20 extends distally of a distal tip 24 of sheath 22.

Transducer assembly 12 has a structure well-known in the art and basically includes, as illustrated in FIGS. 2 and 3, a number of annular piezoelectric disks 26 and thinner annular metal electrodes 28 disposed in a linear array about longitudinal axis 16 and sandwiched between front driver 14 on a distal side and a rear driver 30 on a proximal side. Electrodes 28 are connected to an ultrasonic electrical waveform generator (not shown) whereby the piezoelectric disks undergo alternating expansion and contraction in parallel with the transducer axis 16 to generate an ultrasonic standing wave in probe 18, thereby reciprocating end effector or operative head 20 at a predetermined ultrasonic frequency.

A tubular member 32 coaxial with transducer axis 16 traverses transducer assembly 12 and terminates at a proximal end surface 34 of an internally threaded receptacle 36 provided on a distal end of front driver 14 for receiving an externally threaded connector 38 at a proximal end of probe 18. Proximal end surface 34 is disposed at the acute probe-transducer angle (20°) relative to transducer axis 16. Tubular member 32 serves as a liquid guide channel. Where end effector 20 is a debriding head, tubular member 32 conducts a slurry of irrigant and organic particles away from a surgical site to a debris collector or trap (not shown) and a suction source (not shown). At a proximal end, tubular member 32 is connected to, and passes through, an end cap assembly 40 and carries a fitting 42 for coupling a hose (not shown) that extends to the debris collector. End cap assembly 40 carries an electrical connector 43 for coupling a cable (not shown) from an ultrasonic waveform generator (not shown).

As depicted in FIGS. 2-4 and 6, front driver 14 has an outwardly projecting annular flange 44 (with an O-ring seal 44') at a proximal end and is formed at its distal end with a first cylindrical outer surface 46 coaxial with transducer axis 16. Front driver 14 is further formed with a second cylindrical outer surface 48 at the distal end on a side opposed to cylindrical outer surface 44. Second cylindrical outer surface 48 is coaxial with a longitudinal axis 49 of probe 18. Axes 16 and 49 intersect one another at the probe-transducer angle of 20°. Front driver 14 has two mutually parallel planar outer surfaces or flats 50 and 52 extending parallel to transducer axis 16, each being contiguous with cylindrical outer surfaces 46 and 48 along respective edges or intersection loci 54, 56, 58, 60 (see FIGS. 8 and 9). Front driver 14 further exhibits a trio of mutually contiguous faces or surfaces 62 (FIG. 4), one planar and two cylindrically arcuate, extending between annular flange 44 at a proximal end and inclined cylindrical surface 48 at a distal end.

Figures 6, 7, 8, 9:
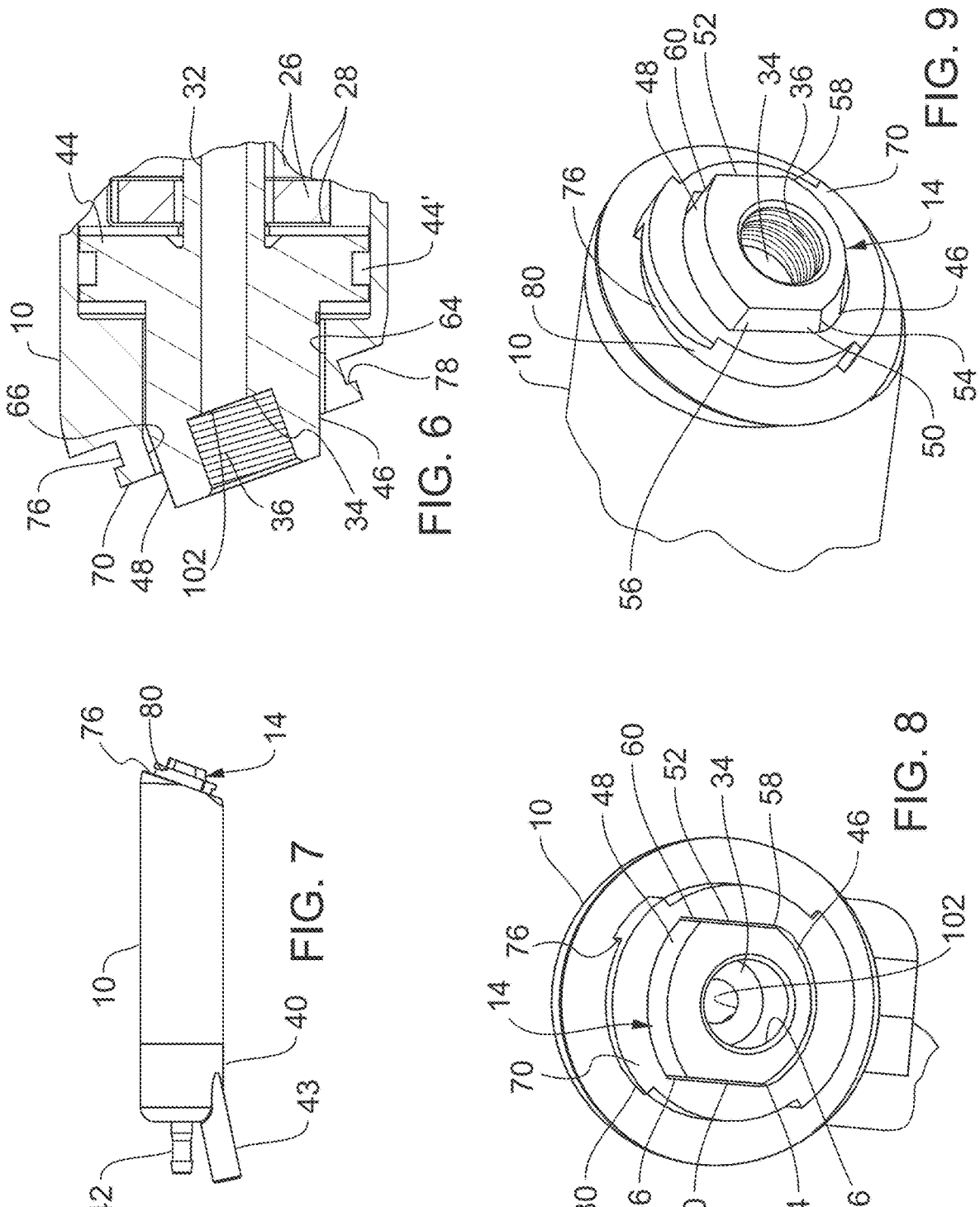
FIG. 6 is longitudinal cross-sectional view of a front driver of the transducer array.
FIG. 7 is a side elevational view of the handpiece casing of FIGS. 1 and 2.
FIG. 8 is a front elevational view of the handpiece casing of FIGS. 1, 2, and 7.
FIG. 9 is a top, side and front perspective view of the handpiece casing of FIGS. 1, 2, 7, and 8.

As best seen in FIG. 6, handpiece casing 10 is formed at a distal end with a cylindrical first internal surface 64 coaxial with transducer axis 16 and a cylindrical second internal surface 66 coaxial with probe axis 49. These surfaces 64 and 66 are disposed in close juxtaposition and mutually parallel relation to front-driver outer surfaces 46 and 48, respectively.

With respect to a coupling of sheath 22 to handpiece casing 10, the sheath is provided at a proximal end with an annular sealing member 96 (FIG. 10) engaging a distal surface 70 (FIGS. 8 and 9) of handpiece casing 10. As described below, sealing member 96 may be implemented as an annular outwardly extending flange of a diaphragm seal 92, when liquid irrigant is fed to a space 88 between sheath 22 and probe 18.

Sheath 22 is provided at a proximal end with a pair of closure or locking elements in the form of two inwardly and radially projecting arcuate flanges or ribs 72 and 74 (FIG. 10) extending in a plane transverse to an axis of the sheath (typically, but not necessarily, probe axis 49). Concomitantly, handpiece casing 10 is formed at its distal end with a cooperating pair of closure or locking elements in the form of two annular open channels or grooves 76, 78 (see FIG. 6) each having one end that is tapered and defined by a respective camming surface 80. Camming surfaces 80 are located along distal sides of the respective annular open channels 76 and face in a proximal direction towards handpiece casing 10.

At least two cooperating sets of closure elements 72, 74 and 76, 78 are disposed on sheath 22 and handpiece casing 10, although three or more may be provided. Annular sealing member 96 is made of a resiliently compressible material such as silicone rubber which exhibits a suitable surface coefficient of friction. Closure elements 72, 74, 76 are mutually configured to frictionally lock sheath 22 to handpiece casing 10 by compression of annular sealing member 96. The locking and the unlocking of sheath 22 to handpiece casing 10 are accomplished by twisting the sheath in opposed angular directions (clockwise, counter-clockwise) relative to the handpiece. Thus the camming mechanism comprising flanges 72 and 74 and respective camming surfaces 80 enables not only a compression-enhanced frictional lock but also enables a quick coupling of sheath 22 to handpiece 10, and a quick de-coupling as well. Thus, handpiece casing 10 may be fixed to sheath 22 by a single locking mechanism consisting of annular sealing member 96, the first closure elements 72 and 74, and the second closure elements 78, 80. Where no liquid irrigant is delivered between sheath 22 and probe 18, sealing member may have a lobed form, in the manner of a clover leaf, or may have a simple circular geometry.

As shown in FIGS. 1 and 2, sheath 22 has two parts, a proximally located main body 82 made of rigid polymeric material and a tapered distal end portion 84 made of a flexible or resilient material such as silicone polymer. Sheath 22 is provided proximate the proximal end with a port or fitting 86 connectable to a source of pressurized liquid coolant (not illustrated) for flowing the coolant into tubular space 88, between probe 18 and an inner surface 90 of the sheath. As shown in FIGS. 2 and 10, diaphragm seal 92 is disposed inside the proximal end of sheath 22 proximally of port or fitting 86. Diaphragm seal 92 has an annular outer surface 93 disposed along inner surface 90 of sheath 22 and is provided at a distal end with an annular inwardly extending flange 94 that circumferentially engages an outer surface (not separately designated) of probe 18 in a liquid-tight seal.

Diaphragm seal 92 has an annular geometry that conforms to the geometry of sheath inner surface 90 at the proximal end of the sheath. Diaphragm seal 92 is preferably spaced in its entirety from probe 18 except at annular inwardly extending flange 94. Diaphragm seal 92 serves to eliminate the painful or distracting sensation that occasionally occurs when a user grasps the proximal end portion of the sheath, as described above. Diaphragm seal 92 is further formed at a proximal end with the annular outwardly extending flange that serves as sealing member 96, clamped between a proximal end surface (not separately referenced in the drawings) of the sheath and distal end surface 70 (FIGS. 6 and 8-10) of handpiece casing 10.

As described above, tubular member 32 extends through transducer assembly 12 to a proximal end surface 34 of threaded receptacle 36. Tubular member 32 has a lumen 100 with a uniform cross-section including at a distal end opening 102 in the plane of receptacle end surface 34. Probe 18 has a longitudinal bore or channel 98 with a proximal end opening 104 of smaller cross-section than that of distal end opening 102 or tubular member 32. Probe bore 98 is aligned with distal end opening 102 of tubular member 32. Lumen 100 and bore or channel 98 together define a continuous passageway that has no shoulder facing in a distal direction at a junction of the tubular member 32 and probe bore 98.

As illustrated in FIGS. 11-14, a cradle 106 for use in manually attaching probe 18 to handpiece casing 10 at an acute angle (e.g., 20°) relative to transducer or handpiece axis 16 comprises a right rectangular prismatic container or frame 108 with an open upper side 110 and a support 112 such as a surface or a cross-bar inside the frame holding the handpiece casing at the acute angle relative to a bottom 114 of the frame. The container or frame 108 is placed on a horizontal surface such as a table top (not shown) with bottom 114 in contact with the horizontal surface. Container or frame 108 is provided with a stabilizer rod or bar 118 that extends outwardly from the container on opposite sides thereof. Stabilizer rod 118 is located with its underside (not separately enumerated) in the plane of cradle bottom 114.

In attaching probe 18 to handpiece casing 10, a user manually screws connector 38 of the probe into receptacle 36. This step may be performed after, but preferably before, the placement of handpiece casing 10 into container or frame 108. Frame 108 has a wall 116 at one end, which serves as a stop engageable with a front or distal end of handpiece casing 10. Wall or stop 116 has a slot 122 which receives a distal end portion of front driver 14, which projects outside of casing 10 (see also FIGS. 8 and 9). Slot 122 allows user access to front driver 14. To tighten probe 18 onto front driver 14 and therefore to casing 10, one pivots a torque wrench 120 (FIG. 14) about probe axis 49 while pressing casing 10 and cradle 108 against the horizontal table top. Stabilizer rod 118 facilitates the application of torque. Wrench 120 is of the kind with a torque detector that automatically arrests further rotation of the wrench about attainment of a preselected amount of torque.

An ultrasonic surgical instrument pursuant to the present invention provides for safe and effective removal of hard tissue such as bone in minimally invasive surgery, under microscope or loop magnification, where the operative end of the instrument is inserted through a tubular retractor or cannula with an internal diameter as small as 18 mm and a probe length of up to 80 mm. The instrument is utilizable with other kinds of retractors. An ultrasonic surgical instrument pursuant to the present invention may have an external diameter in the tissue access area of less than 10 mm, with an instrument working length of up to 165 mm. The angled design (20°) provides a direct line of sight to the instrument distal end compatible with a microscope setup (microscope focal length approx. 300 mm)

An ultrasonic surgical instrument pursuant to the present invention preferably has a combined handpiece and probe length suitable for a full wave (two half-waves) operation at a frequency of approximately 23 KHz, with the angled transition located at approximately ¼-wave length from the proximal end of the handpiece. Thus the resonator assembly may consist of a ¼ wave handpiece and a ¾ wave probe, where the probe connected proximate to the first nodal plane.

The present invention contemplates a viable ultrasonic handpiece-probe assembly with the probe connected to the handpiece at an acute angle in close proximity to a nodal plane. In contrast, the prior art (see U.S. Pat. No. 5,222,937) teaches that an angled connection must be located at an anti-note (loop). Where the handpiece is not angled, the angled feature must occur with the length of the probe or else an angled adaptor must be provided. As set forth in U.S. Pat. No. 5,222,937, a connection at a loop (i.e., anti-node) is necessary to avoid breakage of the "screw-connected portion." It is noted that the motional amplitudes of the present instrument are within the same range (100-300 μm) as the prior art and the assembly does not fracture.

Figures 11, 12, 13, 15:
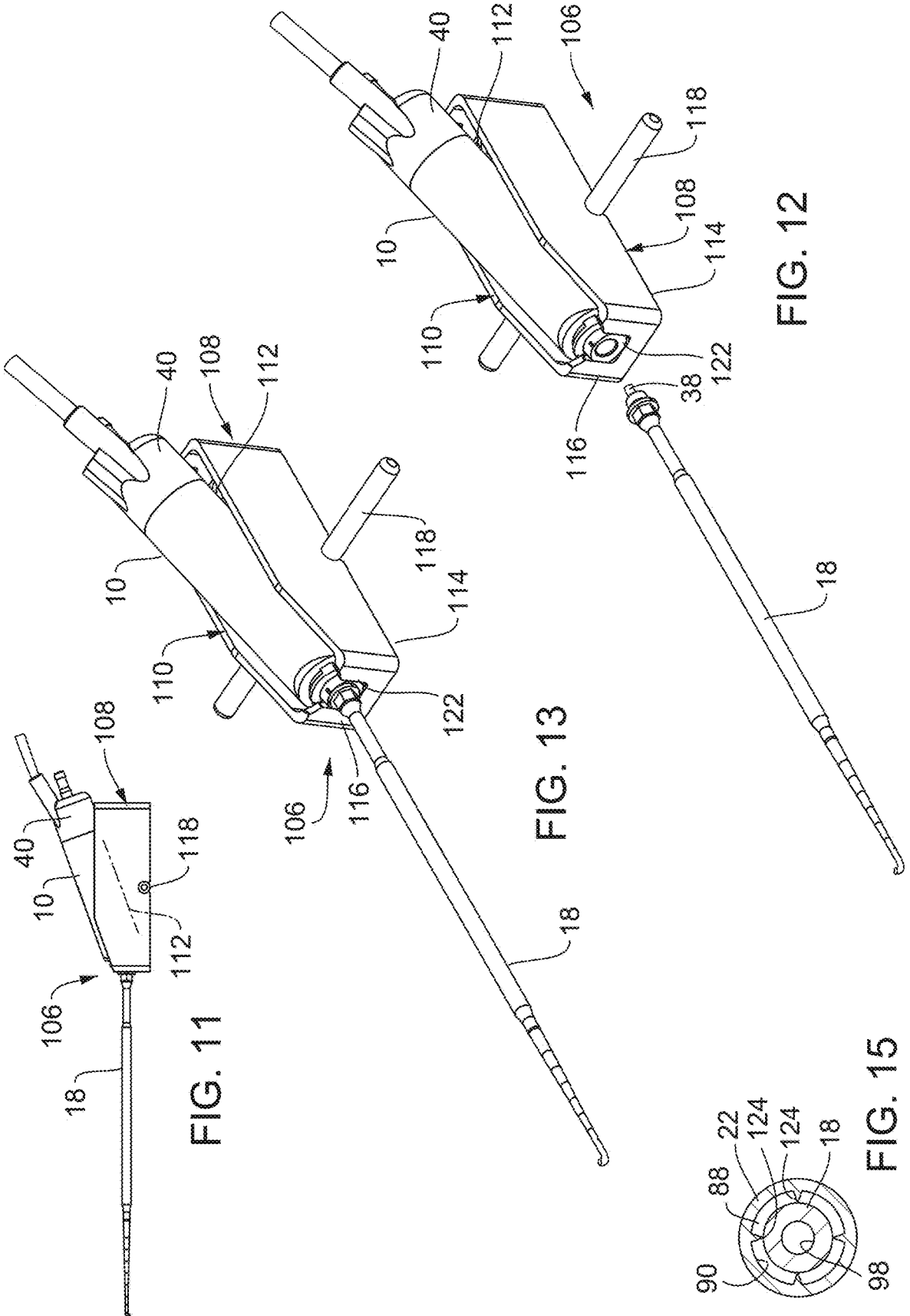
FIG. 11 is a side elevational view of a cradle holding the ultrasonic instrument of FIGS. 1 and 2 in an orientation for manually attaching the probe (e.g., FIGS. 3, 4) to the handpiece casing.
FIG. 12 is a top, front and side partially exploded perspective view of the ultrasonic instrument of FIGS. 1 and 2, showing the handpiece supported in the cradle of FIG. 11 and the probe positioned for attachment.
FIG. 13 is a top, front and side perspective view of the assembled ultrasonic instrument of FIGS. 1 and 2 after attachment of the probe to the handpiece casing.
FIG. 15 is a transverse cross-sectional view taken along line XIII-XIII in FIG. 1.
Figure 14:
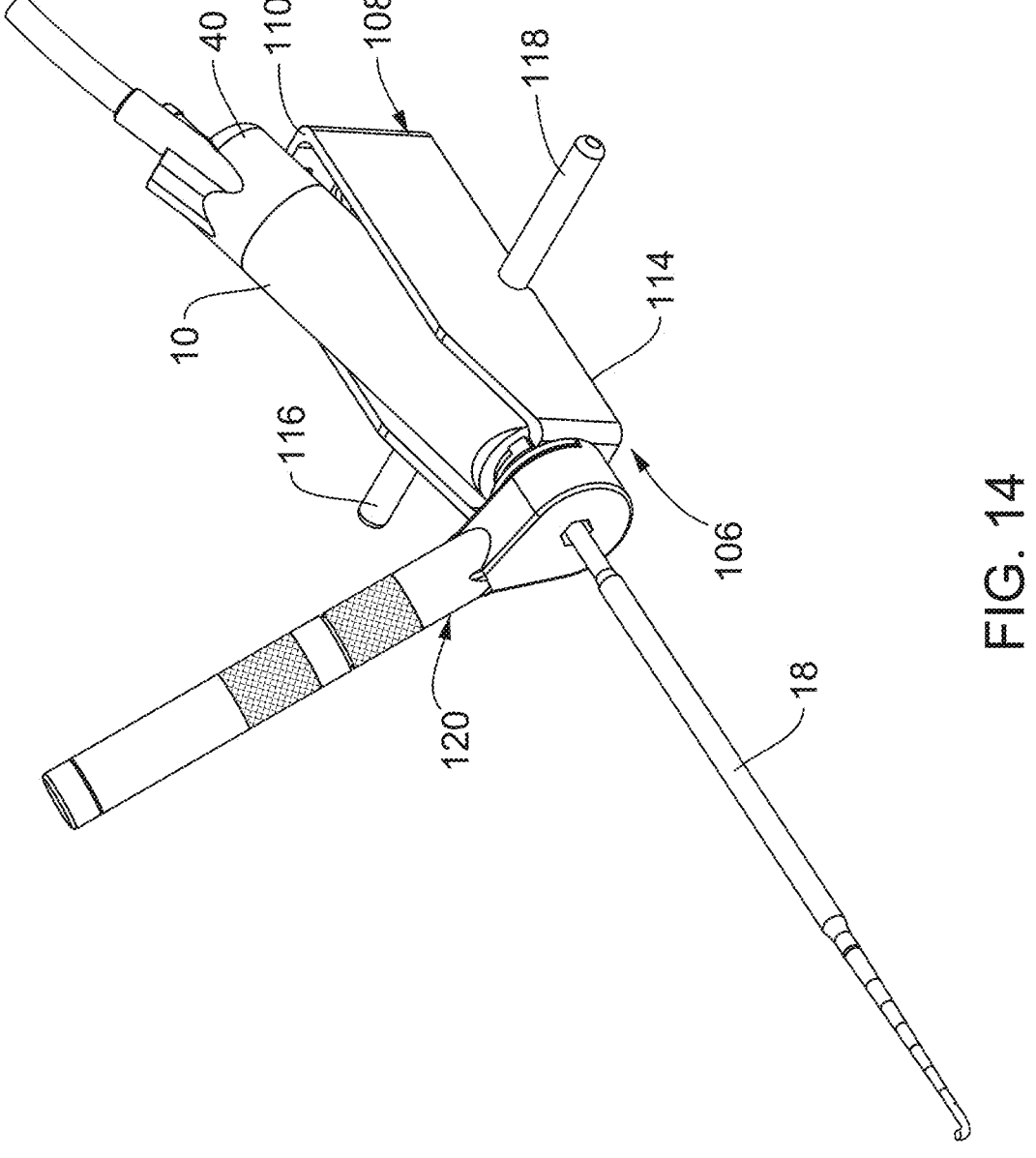
FIG. 14 is a top, front and side perspective view of the cradle and instrument of FIG. 13, also showing a wrench for torquing the probe to the handpiece, or for loosening the probe for removal from the handpiece.

As illustrated in FIG. 15, sheath 22 is provided along inner surface 90 with at least one circular array of circumferentially spaced projections or nubs 124 extending inwardly from surface 90 to the probe 18 to ensure separation or spacing of the sheath and the probe from one another while enabling irrigant flow in a distal direction from port or fitting 86 to distal sheath tip 24. The array of circumferentially spaced projections 124 is positioned proximate to the second nodal plane of the transducer-probe ultrasonic resonator.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

9

What is claimed is:

1. An ultrasonic surgical instrument comprising:
a handpiece;
an electromechanical transducer assembly disposed inside the handpiece, the transducer assembly including a front driver, the transducer assembly having a longitudinal axis;
a probe operatively connected to the front driver at an angle to the longitudinal axis, the probe having a distal end provided with an end effector;
a sheath surrounding the probe and connected at a proximal end to the handpiece, the end effector configured to extend distal to a distal tip of the sheath; and
an annular sealing member configured to engage a portion of a distal surface of the handpiece and be clamped between a proximal surface of the sheath and the distal surface of the handpiece.

2. The ultrasonic surgical instrument defined in claim 1, wherein the probe is connected to the front driver in close proximity to a nodal plane.

3. The ultrasonic surgical instrument defined in claim 1, further including:
at least two first closure elements on a distal surface of the handpiece and a corresponding number of second closure elements on the proximal end of the sheath.

4. The ultrasonic surgical instrument defined in claim 3, wherein the at least two first closure elements include a projection extending in a radial direction, the second closure elements each taking the form of an annular open channel having one tapered end defined by a camming surface.

5. The ultrasonic surgical instrument defined in claim 4, wherein the projections are annular ribs extending in a plane transverse to an axis of the sheath.

6. The ultrasonic surgical instrument defined in claim 4, wherein the camming surface is located along a distal side of the annular open channel and faces in a proximal direction towards the handpiece.

7. The ultrasonic surgical instrument defined in claim 3, wherein the annular sealing member is made of a resiliently compressible material, the at least two first closure elements and the second closure elements being configured to frictionally lock the sheath to the handpiece by compression of the annular sealing member.

8. The ultrasonic surgical instrument defined in claim 7, wherein the handpiece is fastened to the sheath by only one locking mechanism, the only one locking mechanism comprising the annular sealing member, the at least two first closure elements, and the second closure elements.

9. The ultrasonic surgical instrument defined in claim 1, wherein the annular sealing member is radially spaced from a portion of the handpiece and the probe.

10. The ultrasonic surgical instrument defined in claim 1, wherein the ultrasonic transducer assembly is configured to generate ultrasonic vibratory energy at a predetermined frequency that can cause reciprocating movements of the end effector,
the handpiece having a length of a quarter wavelength of the predetermined frequency and the probe having a length of three-quarter wavelengths of the predetermined frequency to facilitate the reciprocating movements of the end effector.

11. The ultrasonic surgical instrument defined in claim 1, wherein the probe includes an externally threaded proximal end, and the front driver includes an internally threaded receptacle at a distal end thereof and configured to receive the externally threaded proximal end of the probe, the internally threaded receptacle having a proximal end surface disposed at an angle relative to the longitudinal axis.

12. An ultrasonic surgical instrument comprising:
a handpiece defining a longitudinal axis;
an electromechanical transducer assembly disposed inside the handpiece, the electromechanical transducer assembly including a front driver;
a probe operatively connected to the front driver at an acute angle to the longitudinal axis, the probe having a distal end provided with an end effector, the electromechanical transducer assembly configured to generate ultrasonic vibratory energy that can be delivered to the probe;
a sheath surrounding the probe and connected at a proximal end to the handpiece, the end effector extending distally of a distal tip of the sheath, the sheath being provided proximate the proximal end with a port connectable to a source of pressurized liquid coolant for flowing the pressurized liquid coolant into a tubular space between the probe and an inner surface of the sheath;
a diaphragm seal disposed near the proximal end of the sheath, the diaphragm seal having an annular outer surface that contacts and forms a liquid-tight seal with the inner surface of the sheath and an annular inwardly extending flange that contacts and forms a liquid-tight seal with the probe, the diaphragm seal configured to reduce sensations experienced by a user grasping a proximal portion of the sheath when the ultrasonic transducer assembly is generating the ultrasonic vibratory energy.

13. The ultrasonic surgical instrument defined in claim 12, wherein the diaphragm is provided at a proximal end with an annular sealing member clamped between a proximal end surface of the sheath and a distal end surface of the handpiece.

14. The ultrasonic surgical instrument defined in claim 12, wherein the diaphragm is spaced from the probe except at the annular inwardly extending flange.

15. The ultrasonic surgical instrument defined in claim 12, wherein the sheath has a main body at a proximal end made of rigid material, the sheath further comprising a distal end portion made of silicone polymer.

16. The ultrasonic surgical instrument defined in claim 12, wherein the front driver has two mutually parallel planar outer surfaces extending parallel to the longitudinal axis of the transducer assembly, each of the two mutually parallel planar outer surfaces being contiguous with a first cylindrical outer surface and a second cylindrical outer surface.

17. The ultrasonic surgical instrument defined in claim 12, wherein the handpiece is formed at a distal end with a cylindrical first internal surface coaxial with the longitudinal axis of the transducer assembly and further formed with a cylindrical second internal surface coaxial with the longitudinal axis of the probe.

18. The ultrasonic surgical instrument defined in claim 12, wherein the probe is connected to the front driver in close proximity to a nodal plane.

19. The ultrasonic surgical instrument defined in claim 12, wherein the ultrasonic transducer assembly is configured to generate ultrasonic vibratory energy at a predetermined frequency that can cause reciprocating movements of the end effector,
the handpiece having a length of a quarter wavelength of the predetermined frequency and the probe having a length of three-quarter wavelengths of the predetermined frequency to facilitate the reciprocating movements of the end effector.

20. The ultrasonic surgical instrument defined in claim 12, wherein the probe includes an externally threaded proximal end, and the front driver includes an internally threaded receptacle at a distal end thereof and configured to receive the externally threaded proximal end of the probe, the internally threaded receptacle having a proximal end surface disposed at an angle relative to the longitudinal axis.

21. An apparatus, comprising:

a handpiece defining a longitudinal axis;

a sheath coupled to a distal end of the handpiece, the sheath defining a lumen;

a probe disposed within the lumen, the probe and the sheath extending from the distal end of the handpiece at an angle relative to the longitudinal axis, the probe including an end effector that is configured to be disposed distal to the sheath when the probe is disposed in the lumen; and an ultrasonic transducer assembly disposed within the handpiece and coupled to the probe, the ultrasonic transducer assembly configured to generate ultrasonic vibratory energy at a predetermined frequency that can cause reciprocating movements of the end effector, the handpiece having a length of a quarter wavelength of the predetermined frequency and the probe having a length of three-quarter wavelengths of the predetermined frequency to facilitate the reciprocating movements of the end effector.

\* \* \* \* \*